(12) United States Patent
Friedman

(10) Patent No.: US 11,617,762 B2
(45) Date of Patent: *Apr. 4, 2023

(54) COMPOSITIONS COMPRISING SULFATED POLYSACCHARIDES

(71) Applicant: SEANERGY DERMATOLOGY LTD., Carme-Yosef (IL)

(72) Inventor: Doron Friedman, Carme-Yosef (IL)

(73) Assignee: Seanergy Dermatology Ltd., Carme-Yosef (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/468,144

(22) PCT Filed: Dec. 10, 2017

(86) PCT No.: PCT/IL2017/051332
§ 371 (c)(1),
(2) Date: Jun. 10, 2019

(87) PCT Pub. No.: WO2018/104950
PCT Pub. Date: Jun. 14, 2018

(65) Prior Publication Data
US 2020/0171075 A1  Jun. 4, 2020

Related U.S. Application Data

(60) Provisional application No. 62/432,628, filed on Dec. 11, 2016.

(51) Int. Cl.
| | |
|---|---|
| *A61K 31/737* | (2006.01) |
| *A61P 29/00* | (2006.01) |
| *A61K 9/48* | (2006.01) |
| *A61K 31/404* | (2006.01) |
| *A61K 31/573* | (2006.01) |
| *A61K 36/02* | (2006.01) |

(52) U.S. Cl.
CPC ............. *A61K 31/737* (2013.01); *A61K 9/48* (2013.01); *A61K 31/404* (2013.01); *A61K 31/573* (2013.01); *A61K 36/02* (2013.01); *A61P 29/00* (2018.01)

(58) Field of Classification Search
CPC ... A61K 31/737; A61K 31/404; A61K 31/573
See application file for complete search history.

(56) References Cited

U.S. PATENT DOCUMENTS

| 9,833,461 | B2 * | 12/2017 | Modi | ................. | A61K 9/06 |
| 2016/0220601 | A1 * | 8/2016 | Klein | ................ | A61K 36/82 |

FOREIGN PATENT DOCUMENTS

WO    WO 2016/056001 A1    4/2016

OTHER PUBLICATIONS

U.S. Appl. No. 16/943,818, filed Jul. 30, 2020, Compositions Comprising Sulfated Polysaccharides, Doron Friedman.
Abraham et al. "Topical Steroid-Damaged Skin" Indian J Dermatol. Sep.-Oct. 2014; 59(5): 456-459.
Adcock et al. "Mechanisms of Steroid Action and Resistance in Inflammation, Corticosteroid-insensitive asthma: molecular mechanisms"Journal of Endocrinology (2003) 178, 347-355.
Arad et al. "The potential of production of sulfated polysaccharides from Porphyridium" Plant and Soil 89,117-127 (1985).
Coondoo et al. "Side-effects of topical steroids: A long overdue revisit" Indian Dermatol Online J. Oct.-Dec. 2014; 5(4): 416-425.
David J Atherton "Topical corticosteroids in atopic dermatitis Recent research reassures that they are safe and effective in the medium term" BMJ vol. 327 Oct. 25, 2003, 942-943.
Firooz et al. "Pimecrolimus Cream, 1%, vs Hydrocortisone Acetate Cream, 1%, in the Treatment of Facial Seborrheic Dermatitis: A Randomized, Investigator-Blind, Clinical Trial" ARCH DERMATOL/ vol. 142, Aug. 2006.
Geresh et al. "The Extracellular Polysaccharides of the Red Microalgae: Chemistry and Rheology" Bioresource Technology 38 (1991) 195-201.
Hajar et al. "A systematic review of topical corticosteroid withdrawal ("steroid addiction") in patients with atopic dermatitis and other dermatoses" J AM ACAD DERMATOL, 2015, 1-9.
https://dailymed.nlm.nih.gov/dailymed/drugInfo.cfm?setid=4881c9b1-b9cf-1b48-e054-00144ff88e88&audience=consumer https://protect-us.mimecast.com/s/ggZNCVONJrl7IBokCzPsjW?domain=dailymed_nlm.nih.gov Feb. 14, 2017.
Humbert et al. "The topical corticosteroid classification called into question: towards a new approach" Experimental Dermatology, 2015, 24, 381-400.
Maria Filomena de Jesus Raposo "Marine Polysaccharides from Algae with Potential Biomedical Applications" Mar. Drugs 2015, 13, 2967-3028.
Patwardhan et al. "Desoximetasone 0.25% Cream and Ointment— an Updated Review of Its Pharmacological Properties and Therapeutic Efficacy in the Treatment of Steroid Responsive Dermatoses" International Journal of Health Sciences & Research (www.ijhsr.org) vol. 7; Issue: 12; Dec. 2017, 290-298.
Spada et al. "Comparative safety and efficacy of topical mometasone furoate with other topical corticosteroids" Australasian Journal of Dermatology (2018) 59, e168-e174.
Procure Hydrocortisone Plus Calendula—hydrocortisone cream, Profoot, Inc.; ProCure Hydrocortisone Cream + Calendula, Feb. 2017, 1-5.

\* cited by examiner

*Primary Examiner* — Pancham Bakshi
(74) *Attorney, Agent, or Firm* — Goodwin Procter LLP

(57) ABSTRACT

The present invention provides a synergistic anti-inflammatory composition comprising one more anti-inflammatory agents such as a steroid, non-steroidal anti-inflammatory drug (NSAID) or a cannabinoid in combination with one or more sulfated polysaccharides. The invention is further directed to a method of treating inflammation and inflammatory diseases using said synergistic composition.

6 Claims, 3 Drawing Sheets

_US 11,617,762 B2_

COMPOSITIONS COMPRISING SULFATED POLYSACCHARIDES

CROSS-REFERENCE TO RELATED APPLICATIONS

This application is a U.S. national stage application under 35 U.S.C. § 371 of International Application No. PCT/IL2017/051332, filed on Dec. 10, 2017, which application claims priority to and the benefit of U.S. Provisional Patent Application No. 62/432,628, filed on Dec. 11, 2016, each of which is incorporated by reference herein in its entirety.

FIELD OF THE INVENTION

The present invention is directed to compositions comprising naturally-occurring substances and methods for their use. More specifically, the compositions of the present invention comprise sulfated polysaccharides in combination with additional anti-inflammatory agents.

BACKGROUND OF INVENTION

Sulfated polysaccharides (SPS) are natural compounds extracted from plants, bacteria and algae and include a complex group of macromolecules with a wide range of important biological activities such as antioxidant, anticoagulant, anticancer, antiviral, anti-allergy, anti-inflammation, antibacterial and anti-biofilm. They occur in the structural elements of both plants and animals, although in plants their distribution is limited to the algae where they may constitute up to 70% of the dry matter of some red seaweeds. The biological features of the SPS known from the prior art include the following properties: antioxidant, antitumor, immunomodulatory, inflammation, anticoagulant, antiviral, antiprotozoal, antibacterial, antilipemic. In addition, SPS are used as dietary fibers and which are degraded only by intestinal flora and are therefore minimally absorbed into the bloodstream in humans.

Mucosal inflammations are usually multimodal diseases, and may often be associated with various bacterial, and/or viral and/or fungal infections. Typically, the affected organ (as well as other organs and tissues) reacts to the presence of the infective agent by means of inflammatory reactions, manifested by redness, edema, discharge, irritation, itching, pain, and allergic type body reactions. In many cases it is difficult and impossible for the physician to diagnose the source of inflammation or infection, whether it is of bacterial, viral, allergen or fungal origin.

For example, conjunctivitis, commonly known as 'red eye' or "pink eye", is one of the most frequent ocular disorders observed in ophthalmic emergency departments. Possible causes include an allergic reaction or an infection of viral or bacterial origin. Using signs and symptoms alone to diagnose conjunctivitis can be misleading—making it difficult for clinicians to differentiate between the viral and bacterial forms of conjunctivitis based upon a clinical exam. Consequently, unnecessary medication (such as antibiotics or steroids to alleviate pain and discomfort) is prescribed.

Another multi-factorial disease is oral mucositis. Oral mucositis is probably the most common, debilitating complication of cancer treatments, particularly chemotherapy and radiation. It can lead to several problems, including pain, nutritional problems as a result of inability to eat, and increased risk of infection due to open sores in the mucosa. Oral mucositis infection is multi modal, and is often associated with bacterial, viral and fungal infections and it is often difficult for the physician to diagnose the source of infection. In addition, in many cases there is co-infection caused by bacteria, viruses and fungi.

Diabetic foot ulcers and ulcerative non-healing wounds are also multi-infection diseases where a biofilm of bacteria and fungi, which forms within the lesion, may retard wound healing. These wounds are difficult to treat due to the multi infection and biofilm formation that is often resistant to many antibiotics. Other multimodal diseases include, for example, various types of skin inflammation and inflammatory bowel disease (IBD).

Steroids are the hallmark of anti-inflammatory medication in a broad range of topical and internal diseases. However, steroid medication is associated with severe side effects, which often limit their use. The dose and duration of the use of steroids is limited due their side effects and hence their efficacy is hampered by their unwanted adverse effects.

United States Patent Application 20130273096 discloses compositions comprising sulfated polysaccharides, which may be used to treat a variety of disorders in subjects by affecting the glycocalyx of a subject in need of such treatment.

United States Patent Application 20160220601 claims "A composition for intravaginal and/or for internal mucosal application, comprising an effective amount of a sulfated polysaccharide, one or more of a natural quaternary polymer, a quaternary molecular compound, a metalloproteinase inhibitor, one or more anti-inflammatory agent, an acid pH control buffering system or any combination thereof, and a pharmaceutically acceptable carrier."

United States Patent Application 20080004236 describes methods and compositions for treating or preventing acute or chronic viral infection over a short time interval in mammals with sulfated polysaccharides.

U.S. Pat. No. 4,465,666 discloses pharmaceutical preparations for the topical treatment of infections caused by herpes viruses, wherein said preparations contain as antiviral agent a synergistic combination of an acid sulfated polysaccharide or acid sulfated polymer.

U.S. Pat. No. 5,668,116 discloses and teaches a method for inactivating viruses which comprises the step of contacting the virus with an effective amount of a substantially pure divalent metal ion chelate of a polysulfate of xylan having glycosidically linked D-glucuronyl side chains with divalent metal ions chelated thereto.

U.S. Pat. No. 5,541,166 discloses and teaches a method of anti-metastatic and/or anti-inflammatory treatment of an animal or human patient comprises administration to the patient of an effective amount of at least one sulfated polysaccharide.

There is a need for a comprehensive medication that will provide a cure for multi-modal infections, will treat bacterial as well as viral infections, avoid biofilm formation and at the same time provide relief from the inflammatory symptoms, such as pain, redness, edema, itching, irritation and discharges.

It is an objective of the present invention to provide an effective anti-inflammatory composition that will provide also anti-microbial and/or anti-viral and anti-biofilm and anti-infection activity.

Another objective of the invention is to provide an effective anti-inflammatory synergistic composition and medication comprising an anti-inflammatory drug, as one of its active components, in which a lower concentration of the anti-inflammatory drug may be used without reduction in their potency or efficacy, and which is associated with reduced adverse and unwanted side effects. It is a further objective of the present invention to provide a medication to alleviate symptoms of inflammation, such as itching, edema, pain and redness resulting from inflammatory conditions of mucosal membrane and skin.

Other objectives and advantages of the present invention will become apparent as the description proceeds.

SUMMARY OF THE INVENTION

The present inventor has unexpectedly discovered that a composition comprising a combination of an anti-inflammatory agent—such as a steroid drug or non-steroid anti-inflammatory drug (NSAID)—together with sulfated polysaccharides is capable of delivering a very strong, synergistic anti-inflammatory effect.

Thus, the present invention is primarily directed to a composition comprising at least one anti-inflammatory agent in combination with at least one sulfated polysaccharide. Preferably, the composition of the present invention also comprises one or more pharmaceutical carriers for treating external and internal mucosal or skin infections and inflammatory diseases.

Preferably, the anti-inflammatory agent(s) and the sulfated polysaccharide(s) are present in relative amounts such that there is a synergistic interaction between said anti-inflammatory agents and said sulfated polysaccharide(s). The term 'synergistic interaction' is used herein to indicate that the anti-inflammatory effect of the combination of the two different agents (i.e. the anti-inflammatory drug or herbal extract and the sulfated polysaccharide) is numerically greater than the sum of the effects caused by the two agents when tested separately (i.e. greater than additive).

In another aspect, the present invention provides a method for treating inflammation and inflammatory diseases of mucosal membranes, skin and body organs, wherein said method comprises the administration of a combination of at least one anti-inflammatory agent or drug such as steroidal drug, cannabinoid compound or a non-steroidal drug (NSAID) with at least one sulfated polysaccharide to a human or animal subject in need of such treatment. Preferably, the combination of these components (i.e. the anti-inflammatory agent(s) and the sulfated polysaccharide(s)) is a synergistic combination, such that the anti-inflammatory effects thereof are greater than the additive results due to said component when used alone.

In one preferred embodiment of this aspect of the present invention, the above-disclosed method comprises administering to a human or mammalian subject any embodiment of the composition of the present invention as defined hereinabove and described in detail hereinbelow.

In one preferred embodiment of this method, the inflammation is associated with one or more conditions selected from the group consisting of infection due to bacteria, viruses or fungi, allergens, cancer, and physical, chemical, autoimmune disease or thermal trauma.

In one preferred embodiment of this method, the inflammation is associated with a disease selected from one or more of a disease, disorder or condition selected from the group consisting of eye diseases, dry eyes, kerato conjunctivitis, wounds, ulcerative and diabetic wounds, oral mucositis, chemotherapy, radiation-induced inflammation, inflammatory bowel diseases, liver diseases, skin infections, skin allergies, psoriasis, mucosal inflammation and gastro-intestinal infections and inflammations, ear diseases or infections, throat or gum inflammations, vaginal inflammation and anal inflammation.

In another aspect, the present invention provides a combination of at least one anti-inflammatory agent or drug such as steroidal drug, cannabinoid compound or a non-steroidal drug (NSAID) with at least one sulfated polysaccharide for use in treating inflammation and inflammatory diseases of mucosal membranes, skin and body organs. Examples of typical inflammatory conditions for which the above-defined combination may be used are given hereinabove.

It has been unexpectedly found that the combination of two groups of compounds—that is, the combination of the anti-inflammatory agent(s) with the sulfated polysaccharide (s)—is a synergistic combination, thereby providing an unexpectedly strong anti-inflammatory effect. Steroids and NSAID are the main drugs used for treating inflammation and inflammatory diseases, and these two classes of agents are the preferred types of anti-inflammatory agents used to prepare the compositions of the present invention.

It is well known in the art that many anti-inflammatory agents, particularly steroids, can cause severe adverse effects that are limiting with regard to the maximum dose that may be used or to the period of treatment. However, the synergistic interaction between the anti-inflammatory agent(s) and the sulfated polysaccharides in the composition of the present invention enables a significant reduction in the concentration of steroids and/or NSAID drugs within said composition or using less potent steroids that bears less severe side effects. This has the effect of reducing the side effects, without loss of the desired anti-inflammatory effects.

The novel composition of the present invention enables the treatment of difficult to treat inflammatory conditions which either arise from infection with bacteria, viruses and/or fungi or are "sterile" inflammations that may be inflicted by an allergen or inflammation resulting from tissue or organ chemical or heat or physical damage. The novel composition provides strong anti-inflammatory effect due to the synergistic nature of the composition while permitting the use of lower concentrations of the anti-inflammatory drugs, or less potent drugs, and hence cause fewer adverse effects while providing the same degree of anti-viral, anti-bacterial and anti-biofilm activities of sulfated polysaccharides, in cases of infection.

As discussed hereinabove, there are several prior art publications which disclose compositions comprising sulfated polysaccharides, sometimes in combination with other agents. However, none of these publications teaches a synergistic combination of an anti-inflammatory drug and a sulfated polysaccharide.

DETAILED DESCRIPTION OF THE INVENTION

Figure 1:
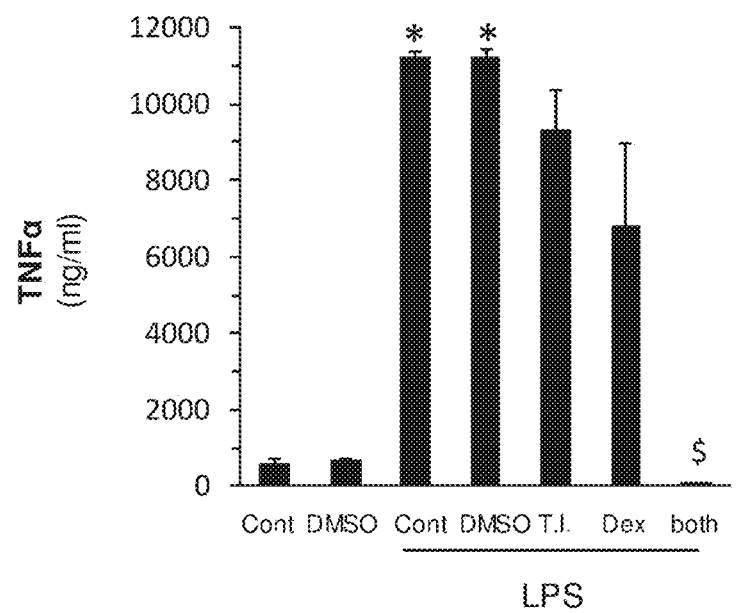
FIG. 1 graphically depicts the synergistic interaction between the SPS and dexamethasone in inhibiting LPS-induced TNFα secretion.

The present invention provides, in one aspect, a composition comprising at least one anti-inflammatory agent in combination with at least one sulfated polysaccharide, wherein there is a synergistic interaction between said anti-inflammatory agent(s) and said sulfated polysaccharide(s) with regard to their anti-inflammatory pharmacological activity.

In another aspect, the invention provides a method for treating inflammation in a human or animal subject in need of such treatment, comprising administering to said subject a synergistic combination of one or more anti-inflammatory agents and one or more sulfated polysaccharides.

In a preferred embodiment of the invention, the weight:weight ratio of the one or more anti-inflammatory agents to the one or more sulfated polysaccharides is in the range of about 1:0.0001-1:100. In another preferred embodiment, this ratio is in the range of about 1:0.001-1:50. In a further preferred embodiment, this ratio is in the range of about 1:0.01-1:20. In yet a further preferred embodiment, this ratio is in the range of about 1:0.1-1:10.

In another embodiment of the composition of the invention, the weight ratio of the anti-inflammatory agent to the sulfated polysaccharide is about 1:0.01. In another embodiment, said ratio is about 1:0.12. In another embodiment, said ratio is about 1:2.78. In another embodiment, said ratio is about 1:0.01. In another embodiment, said ratio is about 1:0.05. In another embodiment, said ratio is about 1:0.69. In another embodiment, said ratio is about 1:1. Similarly, in other preferred embodiments, said ratio may be 1:0.5, 1:0.05, 1:2, 1:0.2 and 1:0.02.

The Anti-Inflammatory Drugs

The one or more anti-inflammatory drugs present in the composition of the present invention are preferably selected from steroidal anti-inflammatory agents, non-steroidal anti-inflammatory drugs (NSAIDs) and anti-inflammatory cannabinoids, and combinations thereof. In the case of steroids, many different such drugs may be used to work the present invention, including (but not limited to) dexamethasone, prednisolone, methylprednisolone, mometasone, halometasone, betamethasone, betamethasone valerate or succinate, fluorocinolone, triamcinolone, clobetasole, diflorazone, loteprednol etabonate, and hydrocortisone and mixtures thereof. Non-limiting examples of NSAIDs include acetaminophen, ibuprofen, diclofenac, aspirin, indomethacin, naproxen, fenoprofen, tolmetin, sulindac, meclofenamate, ketoprofen, piroxicam, tramadol, celecoxib and flurbiprofen, or a salt thereof and mixtures thereof.

Anti-inflammatory agents may be selected from corticosteroids that are the most effective anti-inflammatory therapy for many chronic inflammatory conditions. Corticosteroids (also known as glucocorticosteroids, glucocorticoids or just steroids) are among the most widely used drugs in the world and are effective in many inflammatory and immune diseases.

Most NSAIDs inhibit the activity of cyclooxygenase-1 (COX-1) and/or cyclooxygenase-2 (COX-2), and thereby the synthesis of prostaglandins and thromboxanes. The anti-inflammatory agents used in the current invention may be either approved drugs or herbal medicines and herbal isolated extracts, such as salicylic acid or Devil's Claw (harpagophytum), Licorice and its extracts, Glycyrrhetinic Acid, Chamomile and its extracts, Aloe vera, panthenol, bisabolol, Achillea millefolium extract, Melissa officinalis Leaf Extract, Camellia Sinensis, Wintergreen leaf extract, Calendula Officinalis Extract, Echinacea Purpurea Extract, Cannabis or Hemp Extract, as well as many other herbal materials having anti-inflammatory activity.

In a further preferred embodiment of the invention, the anti-inflammatory agent present in the composition (together with the sulfated polysaccharide) is a cannabinoid. In a particularly preferred embodiment, the cannabinoids are one or more of Cannabidiol (CBD), Cannabidiol acid (CBDA), tetra hydro cannabinol or tetrahydrocannabinolic acid (THC) or (THCA), compounds which have been found to possess a strong anti-inflammatory activity as well as other broad range of different biological activities.

Anti-Inflammatory Drugs Side Effects

Steroids as well as many NSAIDS may cause severe side effects. Thus, for example, NSAIDs (with the exception of aspirin), including both the newer selective COX-2 inhibitors and traditional anti-inflammatories, may increase the risk of myocardial infarction and stroke. Consequently, they are not recommended in those who have had a previous heart attack as they increase the risk of death and/or recurrent MI. The main adverse drug reactions (ADRs) associated with NSAID use relate to direct and indirect irritation of the gastrointestinal (GI) tract. In this regard, NSAIDs cause a dual assault on the GI tract: the acidic molecules directly irritate the gastric mucosa, and inhibition of COX-1 and COX-2 reduces the levels of protective prostaglandins. Inhibition of prostaglandin synthesis in the GI tract causes increased gastric acid secretion, diminished bicarbonate secretion, diminished mucus secretion and diminished trophic effects on epithelial mucosa.

Corticosteroids have been the drugs of choice in treating peritumoral edema in brain cancer patients ever since the 1950s due to their quick onset and efficacy in improving neurologic function. However, long-term use of corticosteroids is known to be accompanied by a myriad of adverse effects that increase with the consumption period.

Potential longer term side effects of taking steroids include inter alia: weakening of the bones (osteoporosis), thin skin that bruises easily, muscle weakness, delayed wound healing, Cushing's syndrome, diabetes, fatty liver diseases and high blood pressure.

Several side effects are also seen during topical treatment with steroids, including: atrophy, striae, rosacea, perioral dermatitis, acne and purpura. Hypertrichosis, pigment alteration, delayed wound healing and exacerbation of skin infections are less frequent. Gastrointestinal steroids side effects are a treatment dose-limiting in inflammatory bowel disease due to severe side effects.

Undesirable side effects of steroids are especially severe in treating auto immune diseases such as Lupus or rheumatoid arthritis (RA) patients, where large doses are often required to control the inflammatory episodes and repeated injections are required due to short duration of drug in blood. In short-term use, GCs are more effective anti-inflammatory agents than nonsteroidal anti-inflammatory drugs (NSAIDs). Long-term systemic treatment with GCs is, however, often accompanied by substantial side effects. These side effects are frequently dose dependent, and are limiting the drug use, with pronounced symptoms observed at high doses and fewer at low doses.

Ophthalmic side effects of steroids include, inter alia, increase in intraocular pressure, glaucoma, and inhibition of wound healing and risk of infections.

Natural products or herbal anti-inflammatory agents are very common, for example, bisabolol, chammazulene, allantoin, licorice extract, curcumin, resveratrol, harpagophytum, caffeic acid, bromelain, grape seed extract, olive leaf extract and quercetin, to name but a few examples. Extensive lists of herbal extracts having anti-inflammatory activity may be found in many different publications that are well known to the skilled artisan in this field.

Sulfated Polysaccharides

Polysaccharides are polymers of simple sugars (monosaccharides) linked together by glycosidic bonds, and they have numerous commercial applications in products such as stabilizers, thickeners, emulsifiers, food, feed, beverages etc.

One common source of sulfated polysaccharides (SPS) is marine algae, with the amount present being found to be differ according to the three major divisions of marine algae: Chlorophyceae (green algae), Rhodophyceae (red algae) and Phaeophyceae (brown algae). The major SPS found in marine algae include fucoidan and laminarans of brown algae, carrageenan of red algae and ulvan of green algae. A comprehensive list of sulfated polysaccharides (SPS) of marine origin is published by Raposo M. F. et al. (2015) [Mar. Drugs, 13(5), 2967-3028; Marine Polysaccharides from Algae with Potential Biomedical Applications]. SP may originate from macroalgae, microalgae, cyanobacteria, Labyrinthulomycetes, and other marine sources.

The SPS may be obtained, for example, from red microalgae such as *Porphyridium* sp., *P. aerugineum, Porphyridium Cruentum, porphyridium purpureum, R. reticulata, Cyanidioschyzon merolae, Atractophora hypnoides, Gelidiella calcicola, Lemanea, Palmaria palmata, Schmitzia hiscockiana, Chondrus crispus, Mastocarpus stellatus,* or *Acrochaetium efflorescens*; brown alga, such as *Undaria pinnatifida, Laminaria saccharina, L. digitata, Fucus evanescens, F. serratus, F. distichus, F. spiralis, Ascophyllum nodosum* and/or *Fucus vesiculosus*; and Green alga-cyanobacteria, for example *Prasinococcus capsulatus Spirulina, Chlorella, Isochrysis* and/or *Dunaliella*.

Methods for the isolation of sulfated polysaccharides are well known in the art. For example, the cultivation of Porphyridium C. and the isolation of extracellular polysaccharides therefrom is described in Arad, S. et al. (1985); Plant and Soil 89: 117-127; "The potential of production of sulfated polysaccharides from Porphyridium. Similarly, a detailed account of the properties of sulfated polysaccharides from red algae may be found in Geresh, S. & Arad, S. (1991) Bioresource Technology 38: 195-201; "The extracellular polysaccharides of the red microalgae: chemistry and rheology".

The SPS used to work the present invention may be of extra-cellular polysaccharide (EPS) origin, cellular origin or cell wall polysaccharides (WPS), and either synthetic or of marine or bacterial origin. Non-limiting examples of SPS that may be used to work the present invention include: carrageenan, heparin, dextran sulfate, pentosan polysulfate, mannan sulfate, dermatan sulfate, heparin super-sulfated, dermatan supersulfated, and agarose-type sulfated polysaccharides produced by marine algae belonging to the class of Phodophyceae (ASP). Regardless of the biological (or synthetic) source, the SPS used in the present invention may be provided in the form of a dry powder, a clear transparent gel product, or an opalescent viscous hydrogel.

In one preferred embodiment, the SPS present in the composition of the present invention is selected from the group consisting of algal sulfated polysaccharides, sulfated polysaccharides of herbal origin, bacterial sulfated polysaccharides and combinations thereof.

In one embodiment, the SPS present in the composition of the present invention is selected from the group consisting of unicellular and multicellular algae.

In one preferred embodiment, the SPS present in the composition of the present invention are branched polysaccharides. In another preferred embodiment, the SPS are linear polysaccharides.

In another preferred embodiment, the SPS are of extracellular origin.

In one embodiment of the invention, polysaccharides or sulfated polysaccharides, may be chemically sulfated to increase the degree of sulfation or chemically, enzymatically or physically processed in order to produce a desired molecular size and or desired sulfation ratio, in order to achieve optimal pharmacological effect.

The SPS used in the present invention may be based on a polysaccharide that is either linear or branched, and may comprise various different sugars, and have different specific degrees of sulfation. The SPS of the present invention are usually heteropolymers, comprising mainly xylose, galactose, and glucose in different proportions. However, other sugars, such as fucose, rhamnose, and fructose, can also be present in the composition of the present invention.

By way of example, the SPS used in the present invention may preferably have a molecular weight in the range of about $10 \times 3$ Dalton to about $10 \times 7$ Dalton, more preferably $10 \times 4$ Dalton to $10 \times 6$ Dalton. However, other sizes of SPS are also possible and form part of the invention as claimed. The SPS, as used in the present invention, may have a viscosity of at least 500 Cps to 10,000 Cps (Centipoise) when prepared as a 1% gel in saline. The viscosity of the SPS may have either Newtonian or non-Newtonian characteristics, pseudoplastic properties, and/or thixotropic characteristics.

The SPS used in the present invention may have a sulfation ratio in the range of about 2 to 25% (calculated as dry matter), more preferably 5 to 15%. The pH value of the SPS in water is generally in the range of 4 to 9, more preferably in the range of 6 to 8.

In one embodiment of the invention, the sulfated polysaccharide is in an aqueous solution, the solution having a concentration of from 0.02 to 2% w/w, and a viscosity of 50 to 20,000 cP at room temperature. In another embodiment the sulfated polysaccharide is resistant to hyaluronidase rendering them resistant to biodegradation and having a longer bioelimination half time.

Inflammatory Diseases and Indications

Inflammatory diseases and conditions are any disease that is associated with inflammation, such as for example eye diseases, including (but not limited to) dry eyes, conjunctivitis, uveitis, pink eyes, keratoconjunctivitis of any origin (including viral, bacterial and allergic); mucositis such as chemotherapy and radiation induced mucositis or gastro intestinal inflammation; inflammatory bowel diseases, ulcerative colitis and Crohn's disease, inflammatory gastric and intestinal ulcers, skin inflammation and skin inflammation associated with dry skin, atopic dermatitis, psoriasis and similar skin diseases; ear, nose and throat infections and non-infective inflammatory conditions; vaginal infections and other vaginal inflammatory conditions; anal or rectal inflammation; inflammation of any tissue or organ that results from physical or chemical insult, from heat, irradiation, auto immune disease or chemotherapy.

The Vehicle Forms

Preferred dosage forms include, but are not limited to, any liquid or semi solid or solid dosage form. The composition may be formulated in a medicament by preparing a topical or mucosal or oral delivery system. The topical delivery system may be in form of eye drops, a suspension, ointment, cream, foam, spray, topical patch. The oral delivery system may be a tablet or capsule or soft capsule or sachet or granules or a syrup. The mucosal delivery system may be a gel, pessary, enema, douche, wash, foam, mucoadhesive gel or tablet for immediate or for slow or controlled release. The vehicle may comprise any acceptable solvent and inactive ingredients as well as preservatives anti-oxidants and coloring agents. The delivery form may be single dose or multiple dose as well as micro particle granulate nano particle microcapsule liposome micelle, and the like as known in the art of pharmaceutical, cosmetic, veterinary medicine and art of formulation. Further details of suitable dosage forms may be obtained from any standard reference work in this field, including, for example: Remington's Pharmaceutical Sciences, Mack Publishing Co, Easton, Pa., USA (1980).

Thus, in some embodiments of the present invention, the composition further comprises one or more excipients selected from the group consisting of solvents, stabilizers, suspending agents, emulsifiers, viscosity agents and combinations thereof.

In some embodiments, the composition of the present invention is formulated as a dosage form selected from the group consisting of a liquid, a suspension, an emulsion, a foam, a spray, a liposome, a semi-solid, a cream, an ointment, a patch, a particulate formulation, a granulate, a micro-particulate formulation, a nano-particulate formulation, a solid dosage form, a tablet, a capsule, an orally-disintegrable capsule, a mouth wash and an adhesive buccal tablet.

In some embodiments, the composition of the present invention is formulated such that the release profile of the composition is selected from the group consisting of immediate, delayed, controlled, sustained and prolonged.

Benefits and Uses of the Present Invention

The anti-inflammatory synergistic composition comprising steroids or NSAID drugs together with sulfated polysaccharides provides many benefits such as increased pharmacological efficacy, use of lower steroid or NSAID concentration, thus having required effect with reduced side effects, prolonged use with less dose or period limits or contra indications due to adverse effects. Moreover, the accompanying anti-viral, anti-bacterial and anti-biofilm activity provides great usability in treating inflammation symptoms in conditions of infectious origin or in subjects prone to infection. The composition may be used to both treat and prevent inflammation of both infectious and non-infectious origin.

Generally, the two main active components of the synergistic combination (i.e. the anti-inflammatory agent and the sulfated polysaccharide) will be administered together in a single composition. In some cases, however, these two components will be administered in separate compositions—either simultaneously (e.g. the patient will swallow two different oral dosage forms, each containing one of the two active components; or will apply two different topical preparations) or consecutively, in either order.

In the case of oral administration, when the anti-inflammatory agent is a steroid, the amount of each of the active components to be administered each day is generally as follows:
  Steroid anti-inflammatory agent: 2-20 mg/day
  Sulfated polysaccharides: 100-4000 mg/day, more preferably 200-1000 mg/day In the case of oral administration, when the anti-inflammatory agent is a non-steroidal anti-inflammatory drug (NSAID), the amount of each of the active components to be administered each day is generally as follows:
  NSAID: 40-400 mg/day
  Sulfated polysaccharides: 100-4000 mg/day, more preferably 200-1000 mg/day In the case of topical administration to the eyes (e.g. by way of eye drops), when the anti-inflammatory agent is a steroid, the concentration of each of the active components within the topical dosage form is as follows:
  Steroid anti-inflammatory agent: 0.1-1.0% (w/w)
  Sulfated polysaccharides: 0.01-1.0%, more preferably 0.05-0.5% (w/w)

In the case of topical administration to the eyes (e.g. by way of eye drops), when the anti-inflammatory agent is an NSAID, the concentration of each of the active components within the topical dosage form is as follows:
  NSAID: 0.1-2.0% (w/w)
  Sulfated polysaccharides: 0.01-1.0%, more preferably 0.05-0.5% (w/w)

In the case of topical administration to the skin (e.g. in a cream, ointment or lotion), when the anti-inflammatory agent is a steroidal anti-inflammatory agent, the concentration of each of the active components within the topical dosage form is as follows:
  Steroid anti-inflammatory agent: 0.05-1.0% (w/w)
  Sulfated polysaccharides: 0.01-2.0%, more preferably 0.05-1.0% (w/w)

In the case of topical administration to the skin (e.g. in a cream, ointment or lotion), when the anti-inflammatory agent is an NSAID, the concentration of each of the active components within the topical dosage form is as follows:
  NSAID: 0.5-2.0% (w/w)
  Sulfated polysaccharides: 0.01-2.0%, more preferably 0.05-1.0% (w/w)

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

In Vitro Working Examples

The objective of the following in vitro experiments was to investigate the compatibility and possible interactions between the Porphyridium C. algae excreted sulfated polysaccharides (SPS), Brown Algae SPS or Green Algae SPS and one of the following anti-inflammatory agents: Dexamethasone, Indomethacin, Hydrocortisone, Mometasone furoate and Diclofenac. The potential for synergistic interaction was tested by assaying inflammatory mediator secretion by a macrophage cell line (RAW 264.7), following stimulation with lipopolysaccharide (LPS). The inflammatory mediators assayed were: tumor necrosis factor—alpha (TNF-alpha), interleukin 6 (IL-6) and prostaglandin E2 (PGE2).

The study was initiated by preliminary cell-viability dose-response analyses to ascertain the maximal concentrations of the compounds tolerated by the cells. Only non-toxic concentrations were used in the following tests.

General Methods:

The commercial sources of the various types of algal polysaccharides used in development of the present invention are as follows: Porphyridium C. extra cellular sulfated polysaccharides may be obtained for example from Frutarom Ltd Israel, ALGUARD™ or from Greensea biotechnologies Ltd France, or from Naturzell Ltd Spain Aqualift™ and others. Undaria pinnafifida extract of sulfated polysaccharide from brown algae is available from Marinova Ltd, Maritech® Australia. *Fucus vesiculosus* extract rich in Fucans is available from Akott Ltd, Akomarine™ or fucoidan from *F. vesiculosus* (Sigma Chemicals, St. Louis, Mo., USA) Laminaran sulfated polysaccharide from Laminaria Digitata and cell wall of green algae (Ulva and Enteromorpha) may be obtained from Elicityl Ltd Olygotech, France. Ulvans and Fucoidans from Carbosynth Ltd, UK. Hi-Q Ltd, Taiwan, Oligo Fucoidan (Low Molecular weight (500 Da) Fucoidan, a sulfated polysaccharide—mainly contains (fucose), extracted from natural marine brown seaweed. Prasinotech Ltd, UK, Glycomar Ltd, EU, MicrA Ltd, Norway, are source of marine green microalgae sulfated polysaccharides.

The concentrations (calculated on a w/w basis) of the test agents selected for the main study were: SPS: 1:4000 (0.0005%); 1:2000 (0.001%); 1:1000 (0.002%); 1:500 (0.004%), Dexamethasone: 0.1 µM (0.0039%), 1 µM (0.039%), 2.5 µM (0.097%), 50 µM (1.95%), Indomethacin: 10 nM (0.00036%), 0.1 µM (0.0036%), 1 µM (0.036%), 2.5 µM (0.089%), 50 µM (1.785%). Hydrocortisone: 5.0 µM (0.18%). Mometasone furoate 0.5 µM (0.026%). Diclofenac: 0.1 µM (0.0039%)

RAW 264.7 monocyte macrophage cells (approximately $4 \times 10^5$/ml) were seeded in 24 well plates containing 800 microliters/well of complete growth medium (DMEM containing 2 mM glutamine, 100 U/ml penicillin and 100 µg/ml streptomycin and 10% fetal bovine serum). The cells were then incubated at 37 degrees Celsius with 5% carbon dioxide for 24 h. At the end of this period, growth medium supplemented with 1 µg/ml lipopolysaccharide (LPS) was added to the cells, together with the test substances (SPS, anti-inflammatory drugs and their combinations) and various controls), and the cells were then incubated for a further 24 hr. period under the same conditions as before. Following this incubation period, the conditioned medium was aspirated from the various test and control wells and centrifuged at 14,000 g for 5 minutes to remove particulate matter. The clear supernatants were then stored at −70 degrees Celsius prior to assaying the inflammatory mediatory content therein.

The cytokine/mediator content in the thawed supernatants was assayed using standard ELISA kits for TNFα, IL-6 and $PGE_2$ (BioLegend Inc., San Diego, Calif., USA).

Example 1

Synergistic Interaction Between Sulfated Polysaccharides and Dexamethasone in Inhibiting TNFα Secretion Method: Raw 264.7 macrophage cells were incubated (as described above) in the absence or presence of LPS and treated without or with the SPS (Porphyridium C. SPS), Dexamethasone or a combination thereof for 24 hr. Then, TNFα levels in the spent medium were quantified by ELISA, as explained above. DMSO were used as vehicle.

Results: The results of this study are shown in FIG. 1. The various treatments are indicated in FIG. 1 by the following annotations: SPS[T.I.] 1:1000; Dexamethasone [Dex] 2.5 µM). As expected, the induction of inflammation by administration of LPS increased the secretion levels of the cytokine. While, at high concentrations, both the commercial steroid drug Dexamethasone and the SPS were able to inhibit the hypersecretion of TNFα, when used alone, the results shown in FIG. 1 clearly indicate that there is synergy of anti-inflammatory action when both agents are used in combination. The results summarized in this figure are shown as the mean of triplicate samples+/−SEM. The statistical significance levels shown in the figure are as follows: *$p<0.05$ for difference from the naïve control. $^S$for synergistic effect.

Example 2

Synergistic Interaction Between Sulfated Polysaccharides and Dexamethasone in Inhibiting IL-6 Secretion Method: Raw 264.7 macrophage cells were incubated (as described above) in the absence or presence of LPS and treated without or with the SPS (Porphyridium C. SPS), Dexamethasone or a combination thereof for 24 hr. Then, IL-6 levels in the supernatant medium were quantified by ELISA, as explained above. DMSO were used as vehicle.

Figure 2:
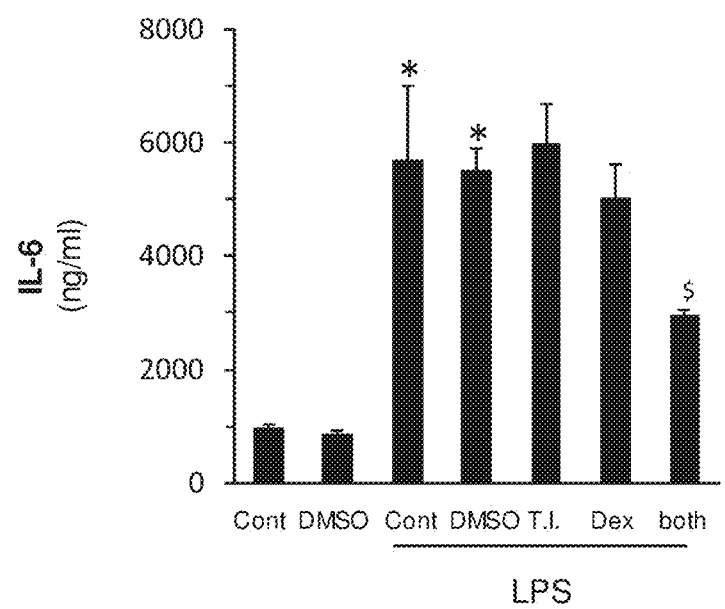
FIG. 2 graphically depicts the synergistic interaction between the SPS and dexamethasone in inhibiting LPS-induced IL-6 secretion.

Results: The results of this study are presented in FIG. 2, in which the various treatments are indicated as follows: TI (SPS 1:4000); Dex (dexamethasone; 0.1 µM). Neither SPS alone nor dexamethasone alone caused a significant decrease in IL-6 secretion. The combination of both of these treatments together, however, caused a much greater than additive inhibitory result, indicating a synergistic interaction between them. The results summarized in this figure are shown as the mean of triplicate samples+/−SEM. The statistical significance levels shown in the figure are as follows: *$p<0.05$ for difference from the naïve control. $^S$for synergistic effect.

Example 3

Synergistic Interaction Between Sulfated Polysaccharides and Indomethacin in Inhibiting Prostaglandin E2 Secretion Method: The effect of the Porphyridium C. SPS was also investigated on Prostaglandin E2 ($PGE_2$) secretion, as an independent inflammation marker derived from arachidonic acid metabolism. Raw 264.7 macrophage cells were incubated (as described above) in the absence or presence of LPS and treated without or with the SPS (Porphyridium C. SPS), Indomethacin or a combination thereof for 24 hr. Then, $PGE_2$ levels in the supernatant medium were quantified by ELISA, as explained above. DMSO were used as vehicle.

Figure 3:
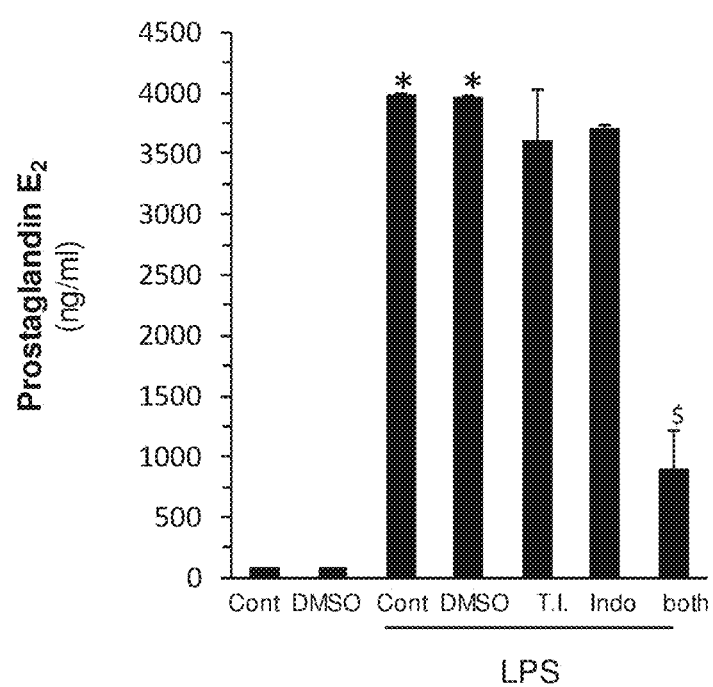
FIG. 3 graphically depicts the synergistic interaction between the SPS, and indomethacin in inhibiting LPS-induced prostaglandin $PGE_2$ secretion.

Results: As seen in FIG. 3, both the SPS and indomethacin (NSAID) inhibited LPS-stimulated Prostaglandin E2 secretion to a certain degree, although this effect was not statistically significant. A synergistic effect was observed when tested in lower concentrations (FIG. 3). The various treatments are indicated as follows: TI (SPS 1:2000); Indo (indomethacin 10 nM). The results summarized in this figure are shown as the mean of triplicate samples+/−SEM. The statistical significance levels shown in the figure are as follows: *$p<0.05$ for difference from the naïve control. $^S$for synergistic effect.

Example 4

Synergistic Interaction Between Sulfated Polysaccharides and Hydrocortisone or Mometasone Furoate in Inhibiting TNFα Secretion Methods: Hydrocortisone, Mometasone furoate and Porphyridium SPS were tested alone and in combination, according to the methods described hereinabove, in order to assess the effect of these various treatments on TNFα secretion in RAW 264.7 cells.

Results: The results of these investigations are summarized below in Table 1:

TABLE 1

| Items | Concentration | TNFα concentration (ng/ml) | % inhibition (mean; n = 3) |
|---|---|---|---|
| Control | Physiological Saline | 11,200 | 0 |
| Poiphyridium SPS | 1:1000 | 9,400 | 16 |
| Hydrocortisone | 5.0 µM | 8,200 | 27 |
| Mometasone furoate | 0.5 µM | 7,600 | 32 |
| Combination of Porphyridium SPS and Hydrocortisone | 1:1000 5.0 µM | 700 | 94 |
| Combination of Porphyridium SPS and Mometasone furoate | 1:1000 0.5 µM | 300 | 97 |

As noted in this table, both of the combinations tested demonstrated a far greater than additive (i.e. synergistic) result for inhibition of TNFα secretion.

Example 5

Synergistic Interactions Between Sulfated Polysaccharides Obtained from Green Algae and Brown Algae and Dexamethasone in Inhibiting TNFα Secretion Methods: Dexamethasone alone, SPS obtained from brown algae and green algae alone, and combinations of dexamethasone with the SPS, were tested, as described hereinabove, in order to assess the effect of these various treatments on TNFα secretion in RAW 264.7 cells.

Results: The results of these investigations are summarized below in Table 2:

TABLE 2

| Items | Concentration | TNFα concentration (ng/ml) | % inhibition |
|---|---|---|---|
| Control | Physiological Saline | 11,200 | 0 |
| Dexamethasone | 1.0 µM | 7,400 | 34 |
| Brown algae SPS | 1:1000 | 8,200 | 27 |
| Green algae SPS | 1:1000 | 9,600 | 14 |
| Combination of Dexamethasone and Brown algae SPS | 1.0 µM 1:1000 | 500 | 96 |
| Combination of Dexamethasone and Green algae SPS | 1.0 µM 1:1000 | 800 | 93 |

As seen in this table, both of the combinations tested demonstrated a far greater than additive (i.e. synergistic) result for inhibition of TNFα secretion, indicating that a variety of different sulfated polysaccharides may be used in combination with anti-inflammatory agents in order to prepare the compositions of the present invention.

Example 6

Synergistic Interaction Between Sulfated Polysaccharides and Diclofenac in Inhibiting TNFα Secretion Methods: Diclofenac alone, SPS obtained from Porphyridium SPS alone, and combinations of diclofenac with the SPS, were tested, as described hereinabove, in order to assess the effect of these various treatments on $PGE_2$ secretion in RAW 264.7 cells.

Results: The results of these tests are summarized below in Table 3:

TABLE 3

| Items | Concentration | $PGE_2$ | % inhibition |
|---|---|---|---|
| Control | Saline | 4,000 | 0 |
| Diclofenac | 0.1 µM | 3,700 | 7.5 |
| Porphyridium SPS | 1:1000 | 3,600 | 10 |
| Combination of Diclofenac and Porphyridium SPS | 0.1 µM 1:1000 | 950 | 76 |

It may be seen from these results that the combination of diclofenac and the sulfated polysaccharide produced a far greater than additive—i.e. synergistic—inhibition of, both of the combinations tested demonstrated a far greater than additive (i.e. synergistic) result for inhibition of $PGE_2$ secretion.

In Vivo Working Example

Example 7

Synergistic In Vivo Anti-inflammatory Effect of a Combination of SPS and Anti-Inflammatory Steroid Method: In this study, BALB/C mice (6 animals in each group) were treated with croton oil on their right ear. The left ear was used as the untreated control. One hour following the croton oil application, the following compositions were applied to the right ears of each mouse, in accordance with their assignment to the various treatment groups:

Group 1—no treatment (control, treated only with croton oil)

Group 2—20 microliters of mometasone furoate 0.1% cream

Group 3—20 microliters of hydrocortisone 1.0% cream

Group 4—10 microliters of Porphyridium SPS 1.0%

Group 5—10 microlites of hydrocortisone 1.0% cream 10 microliters of Porphyridium SPS gel 1.0%

Results: Ear thickness at three hours after the application of the various treatment compositions was measured, and compared with group 1 (untreated control). The percentage reduction of ear skin thickness caused by each treatment modality was then calculated. The results are as follows:

Group 2—65%+/−6%,
Group 3—38%+/−7%
Group 4—20%+/−4%
Group 5—78%.+/−4%

These results indicate that the combination of hydrocortisone and SPS (group 5) caused a greater inhibition of inflammatory edema (as measured by skin thickness) that would be expected from the summation of the results when hydrocortisone and SPS were used alone (groups 3 and 4, respectively). This indicates that the steroid anti-inflammatory agent, hydrocortisone, interacts synergistically with SPS, when tested in an in vivo model of inflammation.

It is important to note that of necessity, relatively low concentrations of SPS where used in the in vitro studies reported hereinabove (Examples 1-6). The reason for this is that at concentrations above about 0.001%, cell viability (as measured by the MTT assay) is compromised. As a result, only low concentrations of SPS could be used in those cell culture studies.

However, it is clear from the results of this in vivo study that the synergistic anti-inflammatory effect of the presently-disclosed composition is also seen when significantly higher concentrations of SPS are used.

Formulation Examples

The following section provides details of several possible formulations containing the composition of the present invention. These formulations are brought for exemplary purposes only, and do not limit the scope of the present invention in any way.

Example 8

Topical Cream Containing Hydrocortisone and Porphyridium SPS

| Ingredient | Formula | | | | | | | |
|---|---|---|---|---|---|---|---|---|
| | A % W/W | B % W/W | C % W/W | D % W/W | E % W/W | F % W/W | G % W/W | H % W/W |
| Hydrocortisone | 1.0 | 1.0 | 1.0 | 1.0 | 0.5 | 0.5 | 0.5 | 0.5 |
| Porphyridium SPS | 1.0 | 0.5 | 0.1 | 0.01 | 1.0 | 0.5 | 0.1 | 0.01 |
| benzyl alcohol | 1.0 | 1.0 | 1.0 | 1.0 | 1.0 | 1.0 | 1.0 | 1.0 |
| glycerin | 3.0 | 3.0 | 3.0 | 3.0 | 3.0 | 3.0 | 3.0 | 3.0 |
| glyceryl monostearate | 2.0 | 2.0 | 2.0 | 2.0 | 2.0 | 2.0 | 2.0 | 2.0 |
| isopropyl palmitate | 6.0 | 6.0 | 6.0 | 6.0 | 6.0 | 6.0 | 6.0 | 6.0 |
| lactic acid | 2.0 | 2.0 | 2.0 | 2.0 | 2.0 | 2.0 | 2.0 | 2.0 |
| paraffin | 6.0 | 6.0 | 6.0 | 6.0 | 6.0 | 6.0 | 6.0 | 6.0 |
| polyoxyl 40 stearate | 3.0 | 3.0 | 3.0 | 3.0 | 3.0 | 3.0 | 3.0 | 3.0 |
| Cetostearyl alcohol | 1.0 | | | | | | | |
| potassium sorbate | 0.5 | 0.5 | 0.5 | 0.5 | 0.5 | 0.5 | 0.5 | 0.5 |
| sorbitan monostearate | 1.0 | 1.0 | 1.0 | 1.0 | 1.0 | 1.0 | 1.0 | 1.0 |
| water | To 100 | To 100 | To 100 | To 100 | To 100 | To 100 | To 100 | To 100 |

Example 9

Topical Cream Containing Undaria SPS and Either Betamethasone Valerate or Mometasone Furoate

| Ingredient | Formula | | | | | | | |
|---|---|---|---|---|---|---|---|---|
| | A % W/W | B % W/W | C % W/W | D % W/W | E % W/W | F % W/W | G % W/W | H % W/W |
| Mometasone furoate | 0.1 | 0.1 | 0.1 | 0.01 | 0.01 | 0.01 | — | — |
| Betamethasone valerate | — | — | — | — | — | — | 0.5 | 0.05 |
| Undaria SPS | 0.5 | 0.1 | 0.01 | 0.5 | 0.1 | 0.01 | 0.1 | 0.01 |
| aluminum starch octylsuccinate | 2.5 | 2.5 | 2.5 | 2.5 | 2.5 | 2.5 | 2.5 | 2.5 |
| hexylene glycol | 3.0 | 3.0 | 3.0 | 3.0 | 3.0 | 3.0 | 3.0 | 3.0 |
| hydrogenated soybean lecithin | 2.0 | 2.0 | 2.0 | 2.0 | 2.0 | 2.0 | 2.0 | 2.0 |
| phosphoric acid | QS | QS | QS | QS | QS | QS | QS | QS |
| white soft paraffin | 4.0 | 4.0 | 4.0 | 4.0 | 4.0 | 4.0 | 4.0 | 4.0 |
| white wax | 4.0 | 4.0 | 4.0 | 4.0 | 4.0 | 4.0 | 4.0 | 4.0 |
| Purified water | To 100 | To 100 | To 100 | To 100 | To 100 | To 100 | To 100 | To 100 |

Example 10

Topical Cream Containing Hydrocortisone and Prasinococcus SPS

A topical cream containing Hydrocortisone and Prasinococcus SPS may be prepared using the following ingredients:

Hydrocortisone 1% and Prasinococcus SPS 0.2% in aloe barbadensis leaf juice, Avena sativa (oat) kernel extract, benzyl alcohol, butylated hydroxytoluene, cetostearyl alcohol, cetyl alcohol, chamomilla recutita (matricaria) flower extract, diazolidinyl urea, dimethicone, distearyldimonium chloride, edetate disodium, glycerin, glyceryl monostearate, hydrolyzed collagen, hydrolyzed elastin, hydrolyzed jojoba esters, jojoba esters, magnesium ascorbyl phosphate, menthyl lactate, methyl gluceth-20, methylparaben, petrolatum, polysorbate 60, potassium hydroxide, PPG-12/SMDI copolymer, propylparaben, purified water, retinyl palmitate, stearamidopropyl PG-dimonium chloride phosphate, steareth-2, steareth-21, stearyl alcohol, tocopheryl acetate

Example 11

Topical Cream Containing Glycyrrhizin and Fucus SPS

A topical cream containing Glycyrrhizin and Fucus SPS may be prepared using the following ingredients:

Glycyrrhizin 1% and Fucus (Fucoidan) SPS 0.5% in Eucerin™ base of Water, Petrolatum, Mineral Oil, Ceresin, Lanolin Alcohol, Phenoxyethanol, Piroctone Olamine

Example 12

Topical Cream Containing Cannabidiol and Ulva SPS

A topical cream containing Cannabidiol and Ulva SPS may be prepared using the following ingredients:

Cannabidiol 1.0%, Ulva (Ulvan) SPS 0.2%, cetearyl octanoate 6.0%, jojoba oil 6.0%, Montanov68™ 4.0%, cetostearyl alcohol 2.0%, glyceryl monostearate 2.0%, sorbitan oleate 1.0%, glycerin 20%, microbial preservative QS, and purified water to 100

Example 13

Topical Ointment Containing Laminaria SPS and Either Dexamethasone or Betamethasone

| | Formula | | | | | |
|---|---|---|---|---|---|---|
| Ingredient | A % W/W | B % W/W | C % W/W | D % W/W | E % W/W | F % W/W |
| Dexamethasone | 0.5 | 0.1 | 0.01 | — | — | — |
| Betamethasone dipropionate | — | — | — | 0.05 | 0.01 | 0.001 |
| Laminaria SPS | 0.5 | 0.1 | 0.01 | 0.5 | 0.1 | 0.01 |
| Mineral oil | 30.0 | 30.0 | 30.0 | 30.0 | 30.0 | 30.0 |
| White petrolatum | To 100 | To 100 | To 100 | To 100 | To 100 | To 100 |

Example 14

Eye Drops Containing Porphyridium SPS and Dexamethasone

Eye drops containing Dexamethasone and Porphyridium SPS may be prepared using the following ingredients:

Dexamethasone phosphate 1 mg/ml and Porphyridium SPS 0.5 mg/ml eye drops, solution, preservative-free, also containing sodium chloride, disodium edetate, disowum phosphate dodecahydrate (E339) and purified water

Example 15

Orally-Disintegrating Tablets Containing Sargassum SPS and Prednisolone

Orally-disintegrable tablets containing Sargassum SPS and Prednisolone may be prepared using the following ingredients:

Orally-disintegrating tablets are prepared in strengths containing 13.4 mg, 20.2 mg, and 40.3 mg prednisolone sodium phosphate (equivalent to 10 mg, 15 mg, or 30 mg prednisolone base, respectively) and 50 mg Sargassum SPS. Each orally disintegrating tablet also contains the following inactive ingredients: citric acid, colloidal silicon dioxide, crospovidone, grape flavor, hypromellose, magnesium stearate, mannitol, methacrylate copolymer, microcrystalline cellulose, sodium bicarbonate, sucralose, and sucrose

Example 16

Controlled-Release Capsules Containing Mesalamine and Porphyridium SPS

Delayed- and extended-release dosage forms of mesalamine with Porphyridium SPS in the form of colon-targeted granules for oral administration may be prepared from the following ingredients:

Capsules containing granules composed of 400 mg mesalamine and 400 mg SPS in a polymer matrix with an enteric coating that dissolves at pH 6 and above.

The inactive ingredients of capsules are colloidal silicon dioxide, magnesium stearate, microcrystalline cellulose, simethicone emulsion ethyl acrylate/methyl methacrylate copolymer nonoxynol 100 dispersion, hypromellose, methacrylic acid copolymer, talc, titanium dioxide, triethyl citrate, aspartame, anhydrous citric acid, povidone, vanilla flavor, and edible black ink.

The same dosage form may also be prepared, but with the mesalamine substituted by either curcumin or cannabidiol.

Example 17

Rectal Foam Containing Hydrocortisone and Fucoidan SPS

An aerosol foam for use in a pressurized canister with an applicator is prepared from the following ingredients:

Hydrocortisone acetate 10% and Fucoidan SPS 1.0% in cetyl alcohol, methyl hydroxybenzoate, propyl hydroxybenzoate, polyoxyethylene-10-stearyl ether, propylene glycol, triethanolamine, purified water, propellant HP 70 and emulsifying wax

Example 18

Oral Cavity Wash Containing Porphyridium SPS and Either Dexamethasone, Cannabidiol or Glycyrrhizin Sterile solutions for use as a mouthwash in the management of conditions such as oral mucositis may be prepared using the ingredients listed in the following table. Citric Acid and/or Sodium Hydroxide may be used to adjust the pH of the final solution to a value in the range of 7.0 to 8.5.

| | Formula | | | |
|---|---|---|---|---|
| Ingredient | A % W/W | B % W/W | C % W/W | D % W/W |
| Dexamethasone sodium phosphate | 1.0 | 0.1 | — | — |
| Cannabidiol | — | — | 1.0 | — |
| Glycyrrhizin | — | — | — | 1.0 |
| Porphyridium SPS | 1.0 | 1.0 | 1.0 | 1.0 |
| Edetate Disodium | 0.01 | 0.01 | 0.01 | 0.01 |

-continued

| Ingredient | Formula | | | |
| --- | --- | --- | --- | --- |
| | A % W/W | B % W/W | C % W/W | D % W/W |
| Sodium Citrate Anhydrous | 1.0 | 1.0 | 1.0 | 1.0 |
| Citric Acid and/or Sodium Hydroxide | Q.S. | Q.S. | Q.S. | Q.S. |
| Water for injection | To 100 | To 100 | To 100 | To 100 |

It will be evident to those skilled in the art that the invention is not limited to the details of the foregoing illustrative example and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A topical composition comprising a steroidal anti-inflammatory agent and an algal sulfated polysaccharide, wherein said steroidal anti-inflammatory agent is present in an amount of 0.1-1.0% (w/w) and the algal sulfated polysaccharide is present in an amount of 0.01-2.0% (w/w).

2. The topical composition of claim 1, wherein the algal sulfated polysaccharide is present in an amount of 0.01-1.0% (w/w).

3. The topical composition of claim 1, wherein the weight ratio of the steroidal anti-inflammatory agent to the algal sulfated polysaccharide is in the range of about 1:0.01-1:20.

4. The topical composition of claim 1, wherein the algal sulfated polysaccharide is of marine origin selected from unicellular and multicellular algae.

5. The topical composition of claim 1, wherein said composition is formulated as a dosage form selected from the group consisting of a liquid, a suspension, an emulsion, a foam, a spray, a liposome, a semi-solid, a cream, an ointment, a patch, a particulate formulation, a granulate, a micro-particulate formulation, and a nano-particulate formulation.

6. A topical composition comprising:
clobetasol;
0.01-2.0% (w/w) algal sulfated polysaccharide; and
an excipient suitable for topical administration.

* * * * *